(12) United States Patent
Wang et al.

(10) Patent No.: US 11,389,564 B2
(45) Date of Patent: Jul. 19, 2022

(54) WHITLOCKITE COATING CONSTRUCTED ON SURFACE OF CALCIUM PHOSPHATE-BASED BIOCERAMIC SUBSTRATE AND PREPARATION METHOD THEREFOR

(71) Applicant: SOUTH CHINA UNIVERSITY OF TECHNOLOGY, Guangdong (CN)

(72) Inventors: Yingjun Wang, Guangdong (CN); Xiaoheng Guo, Guangdong (CN); Naru Zhao, Guangdong (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 347 days.

(21) Appl. No.: 16/605,014

(22) PCT Filed: Nov. 20, 2017

(86) PCT No.: PCT/CN2017/111794
§ 371 (c)(1),
(2) Date: Oct. 14, 2019

(87) PCT Pub. No.: WO2018/188338
PCT Pub. Date: Oct. 18, 2018

(65) Prior Publication Data
US 2021/0100930 A1   Apr. 8, 2021

(30) Foreign Application Priority Data
Apr. 14, 2017   (CN) .......................... 201710242976.3

(51) Int. Cl.
*A61L 27/32* (2006.01)
*A61L 27/10* (2006.01)
*C01B 25/32* (2006.01)

(52) U.S. Cl.
CPC .............. *A61L 27/32* (2013.01); *A61L 27/10* (2013.01); *C01B 25/327* (2013.01); *A61L 2420/02* (2013.01); *C01P 2002/72* (2013.01); *C01P 2004/03* (2013.01)

(58) Field of Classification Search
None
See application file for complete search history.

(56) References Cited

U.S. PATENT DOCUMENTS 5,071,434 A * 12/1991 Tsuzuki ................. A61L 27/32
424/423

FOREIGN PATENT DOCUMENTS

| CN | 103569985 | 2/2014 |
| CN | 103693995 | 4/2014 |
| CN | 104195531 | 12/2014 |
| CN | 107141022 | 9/2017 |
| JP | H09175806 | 7/1997 |

OTHER PUBLICATIONS

"International Search Report (Form PCT/ISA/210) of PCT/CN2017/111794," dated Jan. 25, 2018, with English translation thereof, pp. 1-4.

Wang Yinhai, et al., "Preparation and Characterization of Trace Elements-Codoped Biomimetic Composite Coatings an Pure Titanium Surface," Journal of the Chinese Ceramic Society, vol. 39, Nov. 2011, pp. 1-8.

* cited by examiner

Primary Examiner — Hasan S Ahmed
Assistant Examiner — Randeep Singh
(74) Attorney, Agent, or Firm — JCIPRNET

(57) ABSTRACT

The present invention relates to a method for constructing a whitlockite coating on a surface of a calcium phosphate-based bioceramic substrate and a resulting coating, wherein the preparation method includes the following steps of: preparing pure calcium phosphate-based bioceramic powder firstly, then pre-firing, shaping and calcining the pure calcium phosphate-based bioceramic powder to obtain a calcium phosphate-based bioceramic substrate, placing the substrate in a solution containing $Mg^{2+}$, then transferring the substrate to a high-temperature high-pressure reaction kettle for a hydrothermal reaction, and then cleaning and drying the sample to obtain a whitlockite coating.

12 Claims, 2 Drawing Sheets

WHITLOCKITE COATING CONSTRUCTED ON SURFACE OF CALCIUM PHOSPHATE-BASED BIOCERAMIC SUBSTRATE AND PREPARATION METHOD THEREFOR

CROSS-REFERENCE TO RELATED APPLICATION

This application is a 371 application of International PCT application serial no. PCT/CN2017/111794, filed on Nov. 20, 2017, which claims the priority benefit of Chinese application no. 201710242976.3, filed on Apr. 14, 2017. The entirety of each of the abovementioned patent applications is hereby incorporated by reference herein and made a part of this specification.

BACKGROUND

Technical Field

The present invention belongs to the field of biomedical material preparation, and more particularly, relates to a whitlockite coating constructed on a surface of a calcium phosphate-based bioceramic substrate and a preparation method therefor.

Description of Related Art

As a calcium phosphate-based mineral mainly present in biological bones and teeth, whitlockite ($Ca_{18}Mg_2(HPO_4)_2(PO_4)_{12}$) is the second abundant inorganic mineral in the biological bones, which ranks only second to hydroxyapatite.

At present, there are not many researches on the whitlockite, because the whitlockite has a short existence period in vivo and is difficult to detect on one hand, and on the other hand, it is relatively difficult to synthesize high-purity whitlockite at this stage. Some researchers used $CaCl_2$, $MgCl_2$ and $Na_2HPO_4$ as raw materials to react at 100° C. to prepare whitlockite, while some researchers added $Ca^{2+}$ and $Mg^{2+}$ drop by drop into a phosphate solution to prepare whitlockite. However, the whitlockite prepared by these two methods was accompanied with an impurity phase, so that it is difficult to synthesize pure whitlockite. Of course, with the deepened understanding of scientific researchers on the whitlockite, new breakthroughs were made to the preparation methods. Ki et al. synthesized pure whitlockite by using a $Ca(OH)_2$—$Mg(OH)_2$—$H_3PO_4$ ternary system under the conditions of excess $Mg^{2+}$ and a pH of 4.2. There is also a CN 103569985A patent which used a solution containing Ca ions and solutions of other cations excluding the Ca ions as raw materials, added phosphoric acid in the raw materials, and then aged a cationic aqueous solution containing a phosphoric acid supply material to prepare whitlockite powder. These two methods broken through the synthesis of the whitlockite powder to some extent, but due to the complicated operating conditions and precise experimental requirements, the synthesis process was difficult. In addition, there were no reports on a preparation method of a high-purity whitlockite coating.

A calcium phosphate-based bioactive ceramic has excellent biocompatibility, osteoconductivity, osteoinductivity and biodegradability, and is widely used in a field of biological bone repair. Since the calcium phosphate has a structure similar to that of whitlockite, and the whitlockite is formed on the basis of the calcium phosphate that is added with $(HPO_4)^{2-}$ and $Mg^{2+}$, constructing a whitlockite coating material on a surface of the calcium phosphate becomes a novel method for constructing a surface coating. Based on the structural similarity between the calcium phosphate ceramic and the whitlockite ceramic, the present invention provides a method for preparing a whitlockite coating constructed on a surface of a calcium phosphate ceramic, which effectively realizes the preparation of the whitlockite coating, and precisely regulates and controls a crystal morphology and a crystal size of the whitlockite coating at the same time.

SUMMARY

The present invention is intended to overcome the problem existing in the prior art, and to provide a whitlockite coating constructed on a surface of a calcium phosphate-based bioceramic substrate and a preparation method therefor. A morphology and a size of crystals of a whitlockite coating can be adjusted and controlled by the method.

In order to achieve the objective above, the following technical solutions are used in the present invention.

The objective of the present invention is achieved through the following technical solutions.

A method for constructing a whitlockite coating on a surface of a calcium phosphate-based bioceramic substrate includes the following steps of:

(1) preparing a calcium phosphate-based bioceramic substrate: preparing pure calcium phosphate-based bioceramic powder firstly, and then pre-firing, shaping and calcining the pure calcium phosphate-based bioceramic powder to obtain the calcium phosphate-based bioceramic substrate;

(2) constructing a whitlockite coating on a surface of the calcium phosphate-based bioceramic substrate: placing the calcium phosphate-based bioceramic substrate obtained in the step (1) in a solution containing $Mg^{2+}$, and then transferring the substrate to a high-temperature high-pressure reaction kettle for a hydrothermal reaction; and (3) postprocessing a sample: taking out the sample after the hydrothermal reaction in the step (2) from the reaction kettle, and then cleaning and drying the sample to obtain a whitlockite coating on a surface of the sample.

Preferably, a method for preparing the calcium phosphate-based bioceramic powder in the step (1) is a chemical precipitation method, a hydrothermal method, a sol-gel method, a solid-phase reaction method, an alkoxide method or a precursor method.

Preferably, the calcium phosphate bioceramic in the step (1) is one or more of tricalcium phosphate (α type and β type), hydroxyapatite, tetracalcium phosphate, dicalcium phosphate and other calcium phosphate-based bioceramics.

Preferably, a firing temperature of the pre-firing in the step (1) ranges from 700° C. to 900° C., and a heat preservation time ranges from 2 hours to 4 hours.

Preferably, a method for the shaping in the step (1) is dry pressing shaping, isostatic pressing shaping, plastic shaping, slip casting shaping or extrusion shaping.

Preferably, a firing temperature of the calcining in the step (1) ranges from 900° C. to 1100° C., and a heat preservation time ranges from 2 hours to 4 hours.

Preferably, the solution containing $Mg^{2+}$ in the step (2) is a soluble aqueous solution containing $Mg^{2+}$, such as a simulated body fluid (SBF), a phosphate buffer containing $Mg^{2+}$, a magnesium chloride solution or a magnesium nitrate solution.

Preferably, a pH of the solution containing $Mg^{2+}$ in the step (2) ranges from 5.4 to 7.4; a volume mass ratio of the solution containing $Mg^{2+}$ to the calcium phosphate-based bioceramic substrate ranges from 0.3 L/g to 2.4 L/g; a temperature of the hydrothermal reaction ranges from 80° C. to 120° C., and a time of the hydrothermal reaction ranges from 6 hours to 5 days.

Preferably, the cleaning in the step (3) is to clean the sample with acetone and deionized water in sequence; and the drying is to dry the sample in a drying oven at 40° C. to 50° C.

A whitlockite coating is prepared by the method for constructing a whitlockite coating on a surface of a calcium phosphate-based bioceramic substrate above.

Compared with the prior art, the present invention has the following advantages.

According to the method for constructing a whitlockite coating on a surface of a calcium phosphate-based bioceramic substrate of the present invention, the preparation of a pure whitlockite coating is effectively solved, a crystal morphology and a crystal size of the whitlockite coating are well adjusted and controlled at the same time, with a great promotion significance for expanding the application of biomedical materials.

DESCRIPTION OF THE EMBODIMENTS

To better understand the present invention, the present invention is further described hereinafter with reference to the embodiment, but the protection scope claimed by the present invention is not limited to the scope shown in the embodiments.

Embodiment 1

Figure 1:
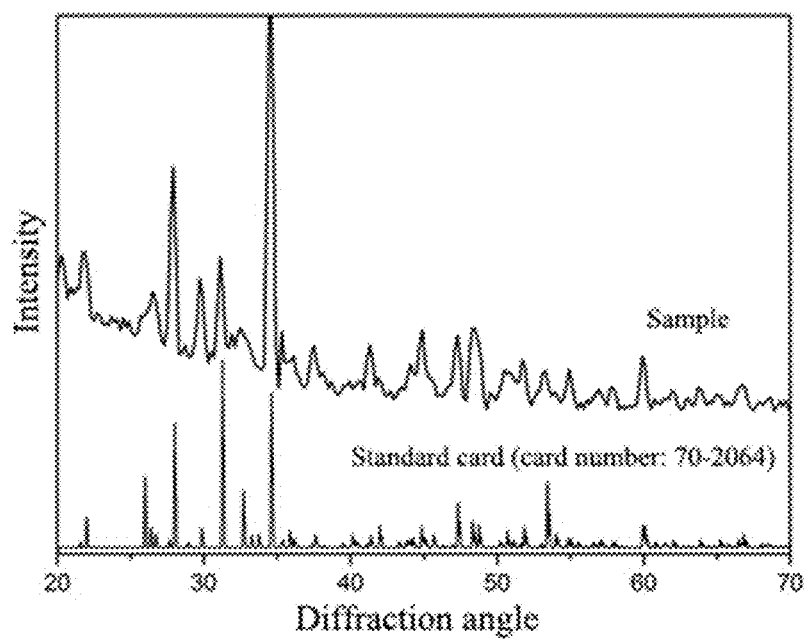
FIG. 1 is an X-ray diffraction (XRD) diagram of a whitlockite coating according to Embodiment 1 of the present invention.
Figure 2:
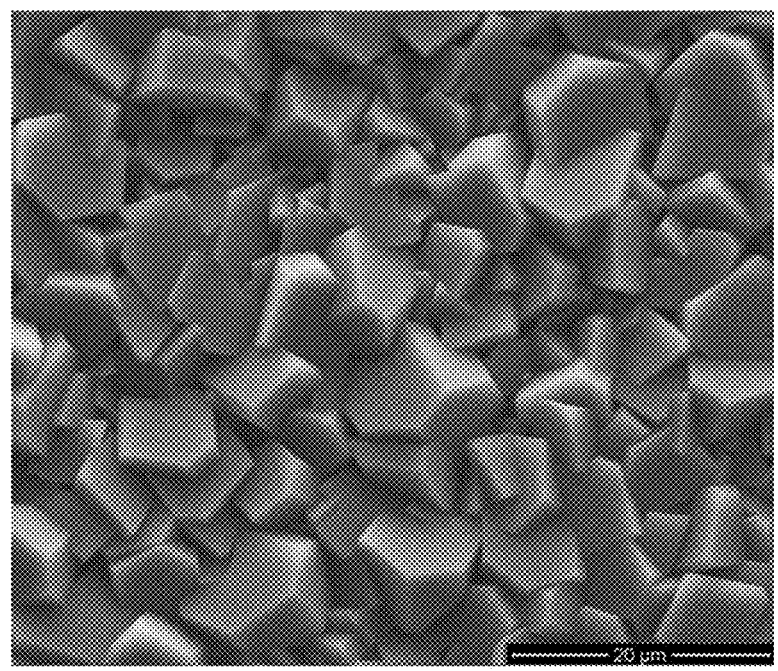
FIG. 2 is a field emission scanning electron micrograph (SEM) of the whitlockite coating in Embodiment 1 of the present invention.

A chemical precipitation method was used, 21.2535 g of $Ca(NO_3)_2 \cdot 4H_2O$ and $(NH_4)_2HPO_4$ were placed in two beakers A and B according to a molar ratio (Ca/P) of 1.5:1, and respectively added with deionized water for full dissolution, a buffer in the beaker B was adjusted to a pH value of 9.0 by using ammonia water with a volume ratio of 1:1, and the solution in the beaker B was dropwise added into the breaker A, and continuously stirred. Meanwhile, a pH value in the dropwise adding process was controlled to be 6.8 by using ammonia water with a volume ratio of 1:1; after the dropwise adding, the mixture was continuously stirred for 12 hours, and then precipitates generated were washed with deionized water for three times and transferred to an oven at 80° C. for drying, and thus pure calcium phosphate bioceramic powder was prepared. The pure calcium phosphate bioceramic powder was pre-fired to 900° C., the temperature was kept for 3 hours, then the pre-fired calcium phosphate bioceramic powder was shaped by dry pressing, i.e., 0.05 g of calcium phosphate bioceramic powder was put into a mold, and a pressure was kept at 1.0 MPa for 2 minutes to obtain a calcium phosphate bioceramic substrate. The calcium phosphate bioceramic substrate was calcined to 1100° C., and the temperature was kept for 3 hours. Then the sample was placed in a simulated body fluid (SBF) with a pH of 7.4, wherein the SBF was prepared according to the following method: 8.035 g of NaCl, 0.355 g of $NaHCO_3$, 0.225 g of KCl, 0.231 g of $K_2HPO_4 \cdot 3H_2O$, 0.311 g of $MgCl_2 \cdot 6H_2O$, 39 ml of 1 M HCl solution, 0.292 g of $CaCl_2$ and 0.072 g of $Na_2SO_4$ were sequentially added into 700 ml of deionized water, and continuously stirred until the sample was completely dissolved, then deionized water was added until the total volume reached 900 ml, then 0.618 g of tris and 1 M HCl solution were added; a pH of the solution was controlled to be 7.42 to 7.45 during the process, and adjusted to be 7.4 after the tris was added completely. Deionized water was added until the total volume reached 1000 ml, and the temperature was controlled to be 36.5° C. during the whole process. Then the sample was transferred to a high-temperature high-pressure reaction kettle for a hydrothermal reaction at 120° C., a volume mass ratio of the SBF to the calcium phosphate bioceramic substrate was controlled to be 2.4 L/g, and the reaction lasted for 4 days. The sample after the hydrothermal reaction was taken out of the reaction kettle, and washed by using acetone and deionized water in sequence; then, the sample was placed in a drying oven at 45° C. for drying to obtain a whitlockite coating on a surface of the sample. See FIG. 1 for X-ray diffraction (XRD) of the whitlockite coating obtained in the present embodiment, wherein x-ray diffraction peaks of the whitlockite coating are corresponding to a standard card one by one, the whitlockite coating has a good crystallinity and a high strength, thus indicating that the pure whitlockite coating is successfully prepared. The whitlockite coating prepared in the present embodiment has a uniform morphology and a uniform grain size, and is shown as a hexagonal plate morphology, and a field emission scanning electron micrograph (SEM) of the whitlockite coating is shown in FIG. 2.

Embodiment 2

Figure 3:
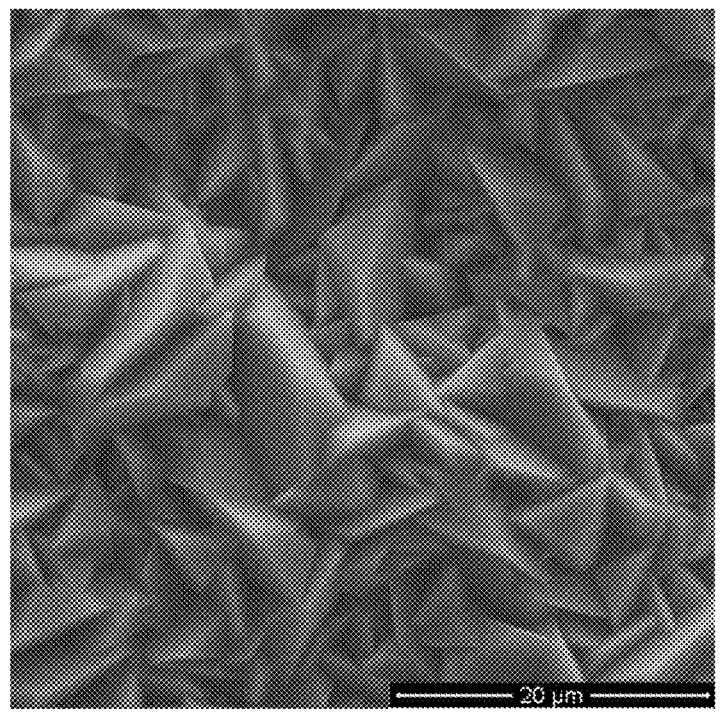
FIG. 3 is a field emission scanning electron micrograph (SEM) of a whitlockite coating in Embodiment 2 of the present invention.

A chemical precipitation method was used, 21.2535 g of $Ca(NO_3)_2 \cdot 4H_2O$ and $(NH_4)_2HPO_4$ were placed in two beakers A and B according to a molar ratio (Ca/P) of 1.5:1, and added with deionized water for full dissolution, a buffer in the beaker B was adjusted to a pH value of 9.0 by using ammonia water with a volume ratio of 1:1, and the solution in the beaker B was dropwise added into the breaker A, and continuously stirred. Meanwhile, a pH value in the dropwise adding process was controlled to be 6.8 by using ammonia water with a volume ratio of 1:1; after the dropwise adding, the mixture was continuously stirred for 12 hours, and then precipitates generated were washed with deionized water for three times and transferred to an oven at 80° C. for drying, and thus pure calcium phosphate bioceramic powder was prepared. The pure calcium phosphate bioceramic powder was pre-fired to 800° C., the temperature was kept for 2 hours, then the pre-fired calcium phosphate bioceramic powder was shaped by dry pressing, i.e., 0.20 g of calcium phosphate bioceramic powder was put into a mold, and a pressure was kept at 2.0 MPa for 3 minutes to obtain a calcium phosphate bioceramic substrate. The calcium phosphate bioceramic substrate was calcined to 1000° C., and the temperature was kept for 2 hours. Then the sample was placed in a simulated body fluid (SBF) with a pH of 7.4, wherein the SBF was prepared according to the following method: 8.035 g of NaCl, 0.355 g of $NaHCO_3$, 0.225 g of KCl, 0.231 g of $K_2HPO_4\cdot 3H_2O$, 0.311 g of $MgCl_2\cdot 6H_2O$, 39 ml of 1 M HCl solution, 0.292 g of $CaCl_2$ and 0.072 g of $Na_2SO_4$ were sequentially added into 700 ml of deionized water, and continuously stirred until the sample was completely dissolved, then deionized water was added until the total volume reached 900 ml, then 0.618 g of tris and 1 M HCl solution were added; a pH of the solution was controlled to be 7.42 to 7.45 during the process, and adjusted to be 7.4 after the tris was added completely. Deionized water was added until the total volume reached 1000 ml, and the temperature was controlled to be 36.5° C. during the whole process. Then the sample was transferred to a high-temperature high-pressure reaction kettle for a hydrothermal reaction at 120° C., a volume mass ratio of the SBF to the calcium phosphate bioceramic substrate was controlled to be 0.6 L/g, and the reaction lasted for 2 days. The sample after the hydrothermal reaction was taken out of the reaction kettle, and washed by using acetone and deionized water in sequence; then, the sample was placed in a drying oven at 45° C. for drying to obtain a whitlockite coating on a surface of the sample. The whitlockite coating prepared in the present embodiment has a uniform morphology and a uniform grain size, and is shown as a triangular plate morphology, and a field emission scanning electron micrograph (SEM) of the whitlockite coating is shown in FIG. 3.

Embodiment 3

Figure 4:
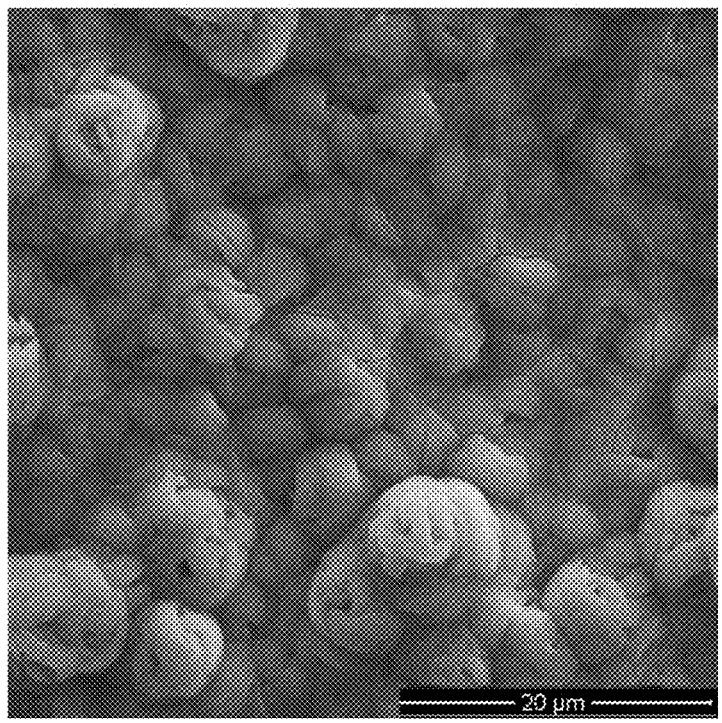
FIG. 4 is a field emission scanning electron micrograph (SEM) of a whitlockite coating in Embodiment 3 of the present invention.

A chemical precipitation method was used firstly, 21.2535 g of $Ca(NO_3)_2\cdot 4H_2O$ and $(NH_4)_2HPO_4$ were placed in two beakers A and B according to a molar ratio (Ca/P) of 1.5:1, and added with deionized water for full dissolution, a buffer in the beaker B was adjusted to a pH value of 9.0 by using ammonia water with a volume ratio of 1:1, and the solution in the beaker B was dropwise added into the breaker A, and continuously stirred. Meanwhile, a pH value in the dropwise adding process was controlled to be 6.8 by using ammonia water with a volume ratio of 1:1; after the dropwise adding, the mixture was continuously stirred for 12 hours, and then precipitates generated were washed with deionized water for three times and transferred to an oven at 80° C. for drying, and thus pure calcium phosphate bioceramic powder was prepared. The pure calcium phosphate bioceramic powder was pre-fired to 700° C., the temperature was kept for 4 hours, then the pre-fired calcium phosphate bioceramic powder was shaped by dry pressing, i.e., 0.15 g of calcium phosphate bioceramic powder was put into a mold, and a pressure was kept at 2.0 MPa for 2 minutes to obtain a calcium phosphate bioceramic substrate. The calcium phosphate bioceramic substrate was calcined to 900° C., and the temperature was kept for 4 hours. Then the sample was placed in a simulated body fluid (SBF) with a pH of 7.4, wherein the SBF was prepared according to the following method: 8.035 g of NaCl, 0.355 g of $NaHCO_3$, 0.225 g of KCl, 0.231 g of $K_2HPO_4\cdot 3H_2O$, 0.311 g of $MgCl_2\cdot 6H_2O$, 39 ml of 1 M HCl solution, 0.292 g of $CaCl_2$ and 0.072 g of $Na_2SO_4$ were sequentially added into 700 ml of deionized water, and continuously stirred until the sample was completely dissolved, then deionized water was added until the total volume reached 900 ml, then 0.618 g of tris and 1 M HCl solution were added; a pH of the solution was controlled to be 7.42 to 7.45 during the process, and adjusted to be 7.4 after the tris was added completely. Deionized water was added until the total volume reached 1000 ml, and the temperature was controlled to be 36.5° C. during the whole process. Then the sample was transferred to a high-temperature high-pressure reaction kettle for a hydrothermal reaction at 80° C., a volume mass ratio of the SBF to the calcium phosphate bioceramic substrate was controlled to be 0.3 L/g, and the reaction lasted for 5 days. The sample after the hydrothermal reaction was taken out of the reaction kettle, and washed by using acetone and deionized water in sequence; then, the sample was placed in a drying oven at 50° C. for drying to obtain a whitlockite coating on a surface of the sample. The whitlockite coating prepared in the present embodiment has a uniform morphology and a uniform grain size, and is shown as a spherical morphology, and a field emission scanning electron micrograph (SEM) of the whitlockite coating is shown in FIG. 4.

The embodiments above are preferred embodiments of the present invention, but the implementations of the present invention are not limited by the embodiments above. Any other amendment, modification, replacement, combination and simplification made without deviating from the spiritual substance and principle of the present invention shall be equivalent substitute modes, which are all included in the protection scope of the present invention.

What is claimed is:

1. A method for constructing a whitlockite coating on a surface of a calcium phosphate-based bioceramic substrate comprising the steps of:
   (1) pre-firing, shaping and calcining a pure calcium phosphate-based bioceramic powder to obtain the calcium phosphate-based bioceramic substrate, wherein the pre-firing is conducted at a temperature ranging from 700° C. to 900° C. for 2 hours to 4 hours, and the calcining is conducted at a temperature ranging from 900° C. to 1100° C. for 2 hours to 4 hours;
   (2) placing the calcium phosphate-based bioceramic substrate in a solution containing $Mg^{2+}$, and then transferring the calcium phosphate-based bioceramic substrate to a reaction kettle for a hydrothermal reaction to obtain a sample, wherein the pH of the solution containing $Mg^{2+}$ ranges from 5.4 to 7.4; the volume mass ratio of the solution containing $Mg^{2+}$ to the calcium phosphate-based bioceramic substrate ranges from 0.3 L/g to 2.4 L/g; the temperature of the hydrothermal reaction ranges from 80° C. to 120° C., and the time of the hydrothermal reaction ranges from 6 hours to 5 days; and
   (3) taking out the sample after the hydrothermal reaction in step (2) from the reaction kettle, and then cleaning and drying the sample to obtain the whitlockite coating on the surface of the sample, wherein the chemical formula of the whitlockite is $Ca_{18}Mg_2(HPO_4)_2(PO_4)_{12}$.

2. The method according to claim 1, wherein the calcium phosphate-based bioceramic powder in step (1) is produced by chemical precipitation.

3. The method according to claim 1, wherein the calcium phosphate bioceramic in step (1) is one or more of tricalcium phosphate, hydroxyapatite, tetracalcium phosphate and dicalcium phosphate.

4. The method according to claim 1, wherein the pure calcium phosphate-based bioceramic powder in step (1) is shaped by dry pressing shaping, isostatic pressing shaping, plastic shaping, slip casting shaping or extrusion shaping.

5. The method according to claim 1, wherein the solution containing $Mg^{2+}$ is a simulated body fluid (SBF), a phosphate buffer containing $Mg^{2+}$, a magnesium chloride solution or a magnesium nitrate solution.

6. The method according to claim 1, wherein the cleaning in step (3) is performed with deionized water in sequence; and the drying is performed in a drying oven at a temperature of 40° C. to 50° C.

7. A whitlockite coating prepared by the method for constructing the whitlockite coating on the surface of the calcium phosphate-based bioceramic substrate according to claim 1.

8. A whitlockite coating prepared by the method for constructing the whitlockite coating on the surface of the calcium phosphate-based bioceramic substrate according to claim 2.

9. A whitlockite coating prepared by the method for constructing the whitlockite coating on the surface of the calcium phosphate-based bioceramic substrate according to claim 3.

10. A whitlockite coating prepared by the method for constructing the whitlockite coating on the surface of the calcium phosphate-based bioceramic substrate according to claim 4.

11. A whitlockite coating prepared by the method for constructing the whitlockite coating on the surface of the calcium phosphate-based bioceramic substrate according to claim 5.

12. A whitlockite coating prepared by the method for constructing the whitlockite coating on the surface of the calcium phosphate-based bioceramic substrate according to claim 6.

\* \* \* \* \*